(12) United States Patent
Katinos

(10) Patent No.: US 11,850,317 B2
(45) Date of Patent: Dec. 26, 2023

(54) STERILIZING ASSEMBLY

(71) Applicant: Alexander Katinos, Plant City, FL (US)

(72) Inventor: Alexander Katinos, Plant City, FL (US)

( * ) Notice: Subject to any disclaimer, the term of this patent is extended or adjusted under 35 U.S.C. 154(b) by 581 days.

(21) Appl. No.: 17/094,245

(22) Filed: Nov. 10, 2020

(65) Prior Publication Data

US 2022/0143234 A1    May 12, 2022

(51) Int. Cl.
*A61L 2/10* (2006.01)
*A61L 2/26* (2006.01)
*B65D 83/02* (2006.01)
*B65G 47/84* (2006.01)

(52) U.S. Cl.
CPC .................. *A61L 2/10* (2013.01); *A61L 2/26* (2013.01); *B65D 83/02* (2013.01); *B65G 47/846* (2013.01); *A61L 2202/11* (2013.01); *A61L 2202/122* (2013.01); *A61L 2202/14* (2013.01); *B65G 2203/0266* (2013.01); *B65G 2203/042* (2013.01)

(58) Field of Classification Search
CPC ....................................................... A61L 2/26
See application file for complete search history.

(56) References Cited

U.S. PATENT DOCUMENTS

| | | | |
|---|---|---|---|
| 6,039,928 A | 3/2000 | Roberts | |
| 8,058,629 B2 | 11/2011 | Long | |
| 8,337,770 B2 | 12/2012 | Wind | |
| 8,357,914 B1 | 1/2013 | Caldwell | |
| 9,511,160 B1 | 12/2016 | Wind | |
| 2009/0148358 A1* | 6/2009 | Wind | A61L 2/10 422/186.3 |
| 2009/0206101 A1* | 8/2009 | Friesen | B26D 1/42 221/12 |
| 2014/0245866 A1* | 9/2014 | Hadlock | A61L 2/10 81/9.2 |
| 2014/0263394 A1* | 9/2014 | Horian | A47G 21/12 221/192 |
| 2017/0151825 A1 | 6/2017 | McDowell | |
| 2022/0092947 A1* | 3/2022 | Steadman | B42D 25/29 |

FOREIGN PATENT DOCUMENTS

WO    WO2016114883    7/2016

* cited by examiner

*Primary Examiner* — Gene O Crawford
*Assistant Examiner* — Ayodeji T Ojofeitimi

(57) ABSTRACT

A sterilizing assembly for on-demand dispensing of sterilized writing utensils includes a housing, which defines an interior space. The housing has a first slot and a second slot positioned in a top and a bottom thereof, respectively. A sanitizing unit and a dispensing unit are engaged to the housing and are positioned in the interior space. The sanitizing unit sterilizes a contaminated writing utensil inserted into the housing through the first slot. The dispensing unit will dispense a sterilized writing utensil from the housing through the second slot. A sensor engaged to the bottom of the housing detects a presence of a hand proximate to the second slot. The sensor is operationally engaged to the dispensing unit and thus is positioned to signal the dispensing unit to dispense the sterilized writing utensil.

13 Claims, 4 Drawing Sheets

STERILIZING ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention

The disclosure relates to sterilizing assemblies and more particularly pertains to a new sterilizing assembly for on-demand dispensing of sterilized writing utensils.

(2) Description of Related Art Including Information Disclosed Under 37 CFR 1.97 and 1.98

The prior art relates to sterilizing assemblies for writing utensils, which may comprise containers having an ultraviolet light positioned therein, which also may have inlet and outlet slots positioned therein with a guide channel extending therebetween.

BRIEF SUMMARY OF THE INVENTION

An embodiment of the disclosure meets the needs presented above by generally comprising a housing, which defines an interior space. The housing has a first slot and a second slot positioned in a top and a bottom thereof, respectively. A sanitizing unit and a dispensing unit are engaged to the housing and are positioned in the interior space. The sanitizing unit is configured to sterilize a contaminated writing utensil inserted into the housing through the first slot. The dispensing unit is configured to dispense a sterilized writing utensil from the housing through the second slot. A sensor engaged to the bottom of the housing is configured to detect a presence of a hand proximate to the second slot. The sensor is operationally engaged to the dispensing unit and thus is positioned to signal the dispensing unit to dispense the sterilized writing utensil.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
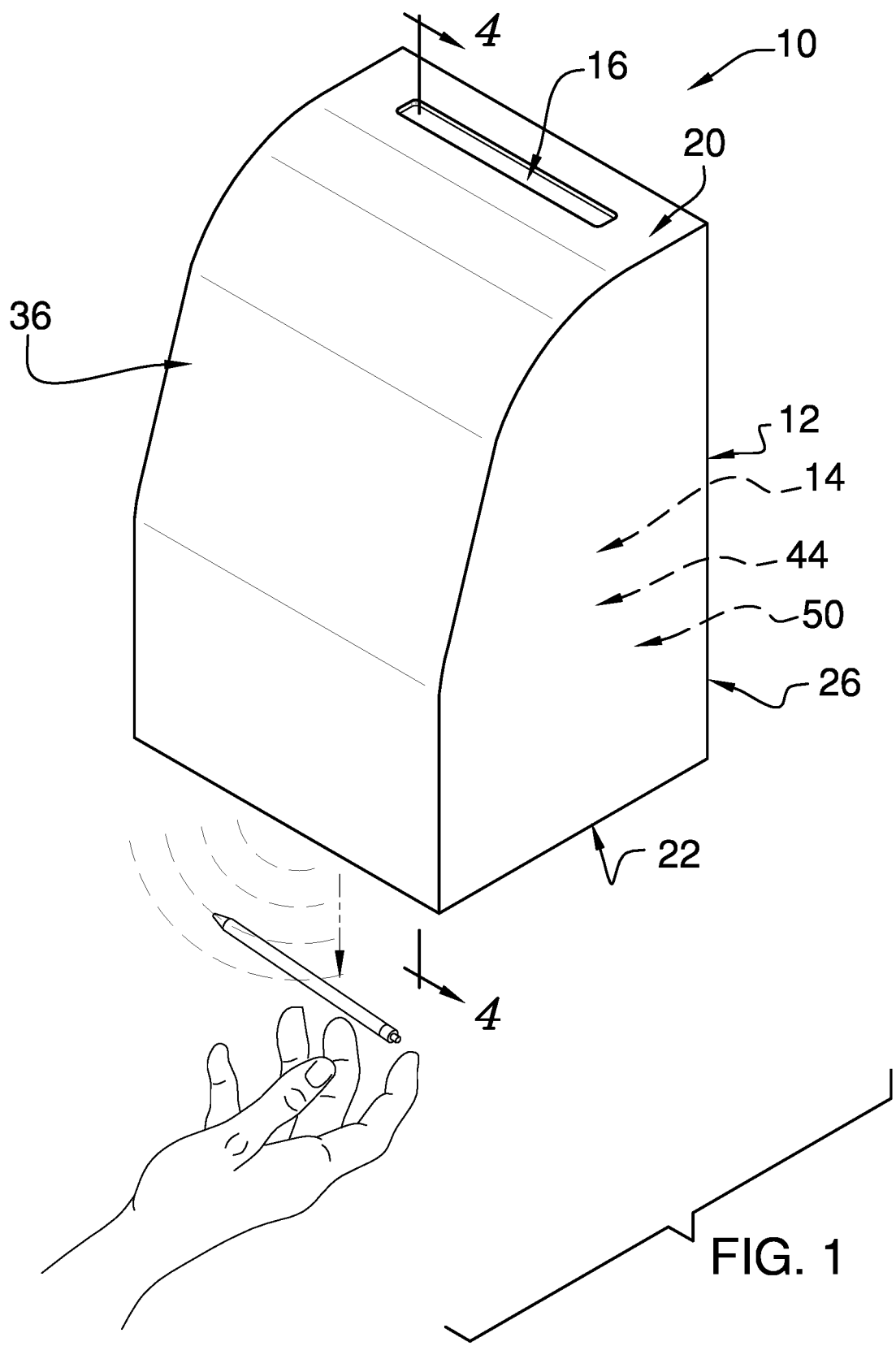
FIG. 1 is an in-use view of a sterilizing assembly according to an embodiment of the disclosure.

With reference now to the drawings, and in particular to FIGS. 1 through 4 thereof, a new sterilizing assembly embodying the principles and concepts of an embodiment of the disclosure and generally designated by the reference numeral 10 will be described.

As best illustrated in FIGS. 1 through 4, the sterilizing assembly 10 generally comprises a housing 12, which defines an interior space 14. The housing 12 has a first slot 16 and a second slot 18 positioned in a top 20 and a bottom 22 thereof, respectively. The housing 12 has a set of keyhole slots 24 positioned in a back 26 thereof. The keyhole slots 24 are configured for selective insertion of mounting hardware (not shown) to affix the housing 12 to a substantially vertical surface.

A set of panels 28 is engaged to the housing 12 defining a reservoir 30, an upper chamber 32, and a lower chamber 34 within the interior space 14. The first slot 16 opens into the reservoir 30. The reservoir 30 is positioned adjacent to the top 20 and the back 26 of the housing 12. The upper chamber 32 is positioned adjacent to the top 20 and a front 36 of the housing 12. The lower chamber 34 extends from the reservoir 30 and the upper chamber 32 to the bottom 22 of the housing 12. Respective panels 28, which separate the reservoir 30 and the lower chamber 34 from the upper chamber 32, are substantially transparent. The reservoir 30 is V-shaped adjacent to a lower limit 38 thereof, when viewed from a respective opposed side 40 of the housing 12. The lower limit 38 has a third slot 42 positioned therein, which functions to fluidically engage the reservoir 30 and the lower chamber 34.

A sanitizing unit 44 is engaged to the housing 12 and is positioned in the interior space 14. The sanitizing unit 44 is configured to sterilize a contaminated writing utensil inserted into the housing 12 through the first slot 16. The sanitizing unit 44 comprises a light emitting diode 82, which is configured to emit ultraviolet light. The sanitizing unit 44 comprises a first ultraviolet emitter 46, which is positioned in the upper chamber 32 and is configured to direct ultraviolet light into the lower chamber 34. The first ultraviolet emitter 46 may emit at 150-170 nanometers.

The sanitizing unit 44 also may comprise a second ultraviolet emitter 48, which is positioned in the upper chamber 32 and is configured to direct ultraviolet light into the reservoir 30. The second ultraviolet emitter 48 may emit at 150-170 nanometers.

A dispensing unit 50 is engaged to the housing 12 and is positioned in the interior space 14. The dispensing unit 50 is configured to dispense a sterilized writing utensil from the housing 12 through the second slot 18.

The dispensing unit 50 comprises an axle 52, which is positioned in the lower chamber 34 and which is rotationally engaged to and extends between the opposed sides 40 of the housing 12. A hub 54 is engaged to the axle 52. A plurality of spokes 56 is engaged to and extends radially from the hub 54 to define a plurality of channels 58. Each channel 58 extends longitudinally along the hub 54 and is positioned to receive a respective writing utensil when it passes through the third slot 42 from the reservoir 30 into the lower chamber 34.

A motor 60 is engaged to the housing 12 and is positioned in the lower chamber 34. A belt 62 is engaged to and extends between a shaft 64 of the motor 60 and the axle 52. The motor 60 is positioned to selectively turn the hub 54 to selectively align a respective channel 58 with the second slot 18 so that the dispensing unit 50 is configured to dispense a sterilized writing utensil through the second slot 18 into a hand of a user.

A cover plate 66 is engaged to the housing 12 and extends arcuately from the second slot 18 toward the front 36 of the housing 12 and proximate to the plurality of spokes 56. The cover plate 66 is configured to retain the sterilized writing utensil within the respective channel 58 until the respective channel 58 is substantially aligned with the second slot 18.

A sensor 68 engaged to the bottom 22 of the housing 12 is configured to detect a presence of the hand proximate to the second slot 18. The sensor 68 is operationally engaged to the dispensing unit 50 and thus is positioned to signal the dispensing unit 50 to dispense the sterilized writing utensil. The sensor 68 is configured to detect motion proximate to the second slot 18 or an object, such as the hand, positioned proximate to the second slot 18.

The present invention is anticipated to be useful is preventing the spread of communicable diseases transmitted through the handling of writing utensils. For example, an assembly 10 could be positioned in a setting where writing utensils are used by persons for filling out forms, such as a doctor's or dentist's office, a pharmacy, government offices, and the like. A user would simply place their hand by the sensor 68 to obtain a sterilized writing utensil from the second slot 18. Upon completing a form or forms, the user would insert the contaminated writing utensil through the first slot 16 into the reservoir 30, where it would again be sterilized.

A power supply unit 70 is engaged to the housing 12 and is positioned in the interior space 14. The power supply unit 70 is operationally engaged to the sanitizing unit 44, the dispensing unit 50, and the sensor 68, to supply power thereto. The power supply unit 70 may comprise an AC to DC inverter 72, a socket 74, and a power cord 76. The socket 74 is positioned in a respective opposed side 40 of the housing 12 and is operationally engaged to the AC to DC inverter 72. The power cord 76 is configured to operationally engage the AC to DC inverter 72 to a source of alternating current. The present invention also anticipates the power supply unit 70 comprising a battery (not shown).

Figure 2:
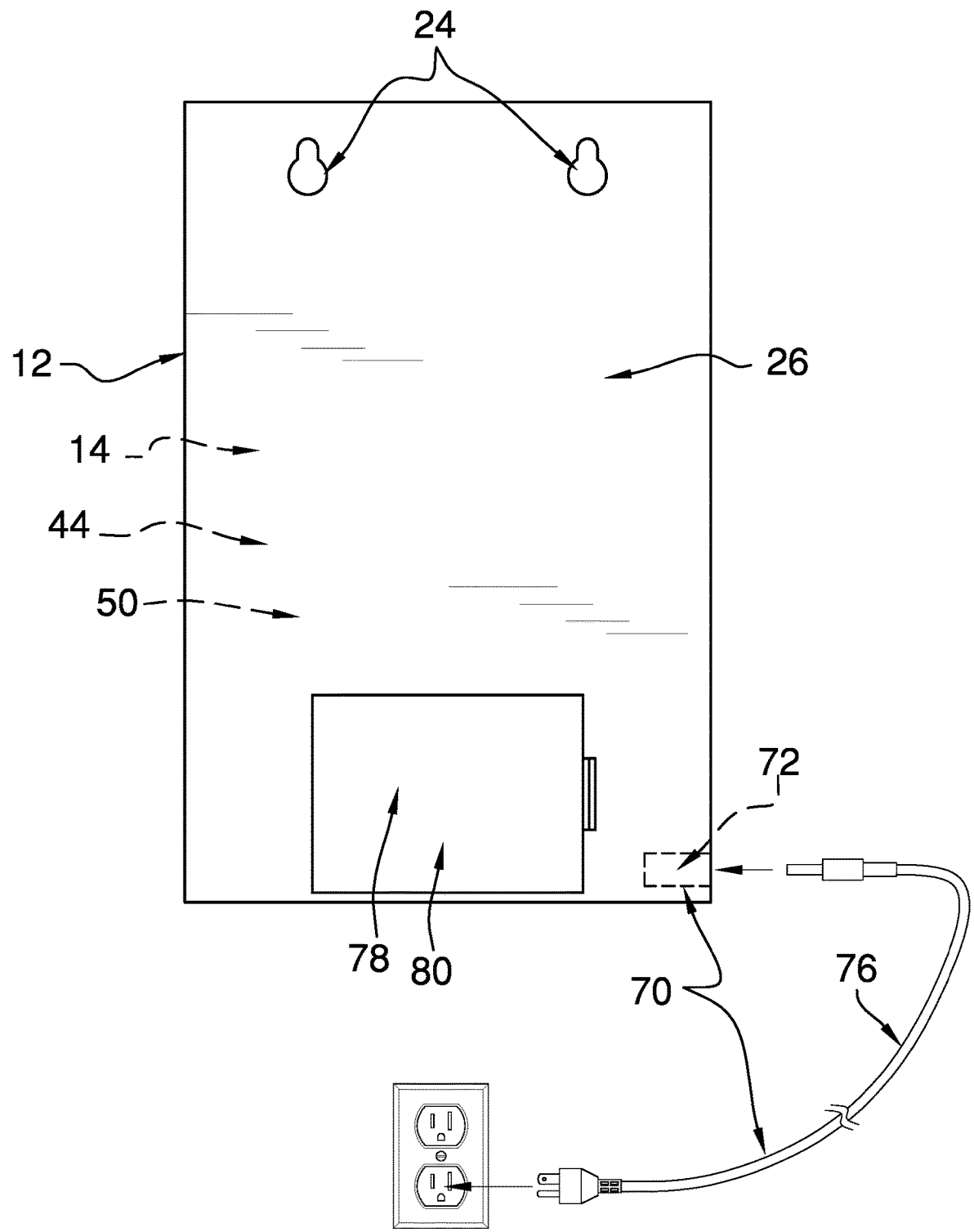
FIG. 2 is a back view of an embodiment of the disclosure.
Figure 3:
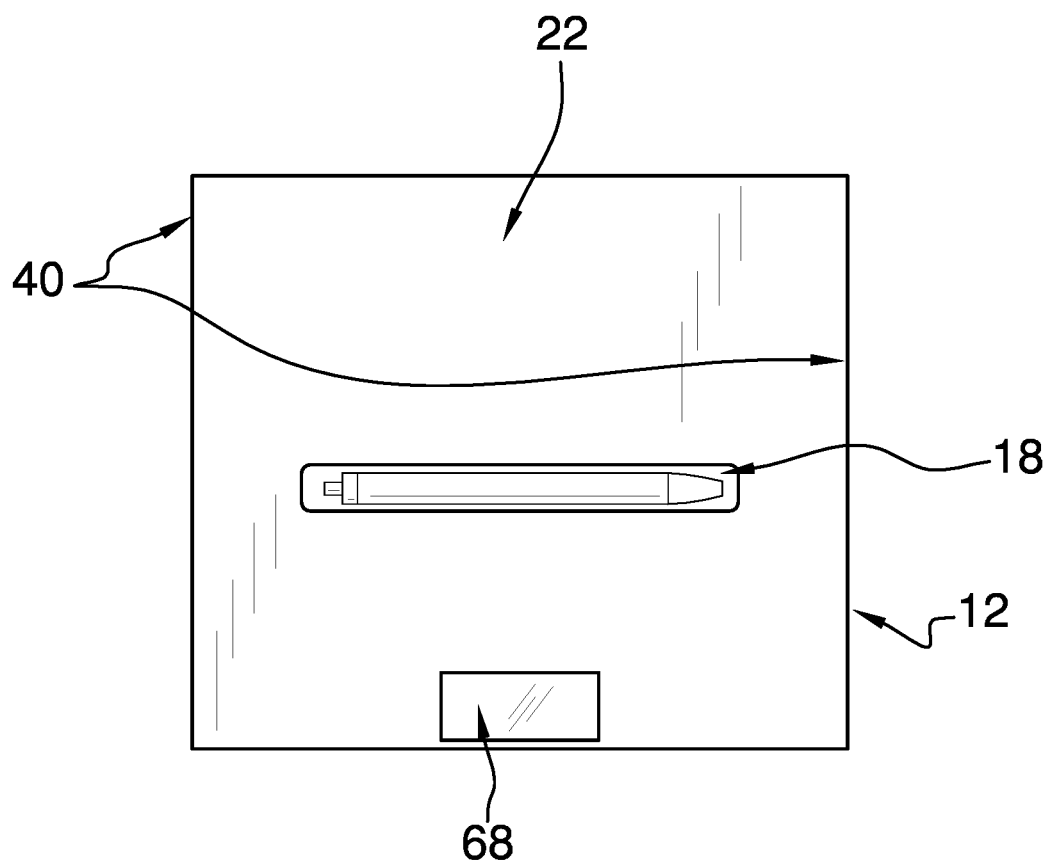
FIG. 3 is a bottom view of an embodiment of the disclosure.
Figure 4:
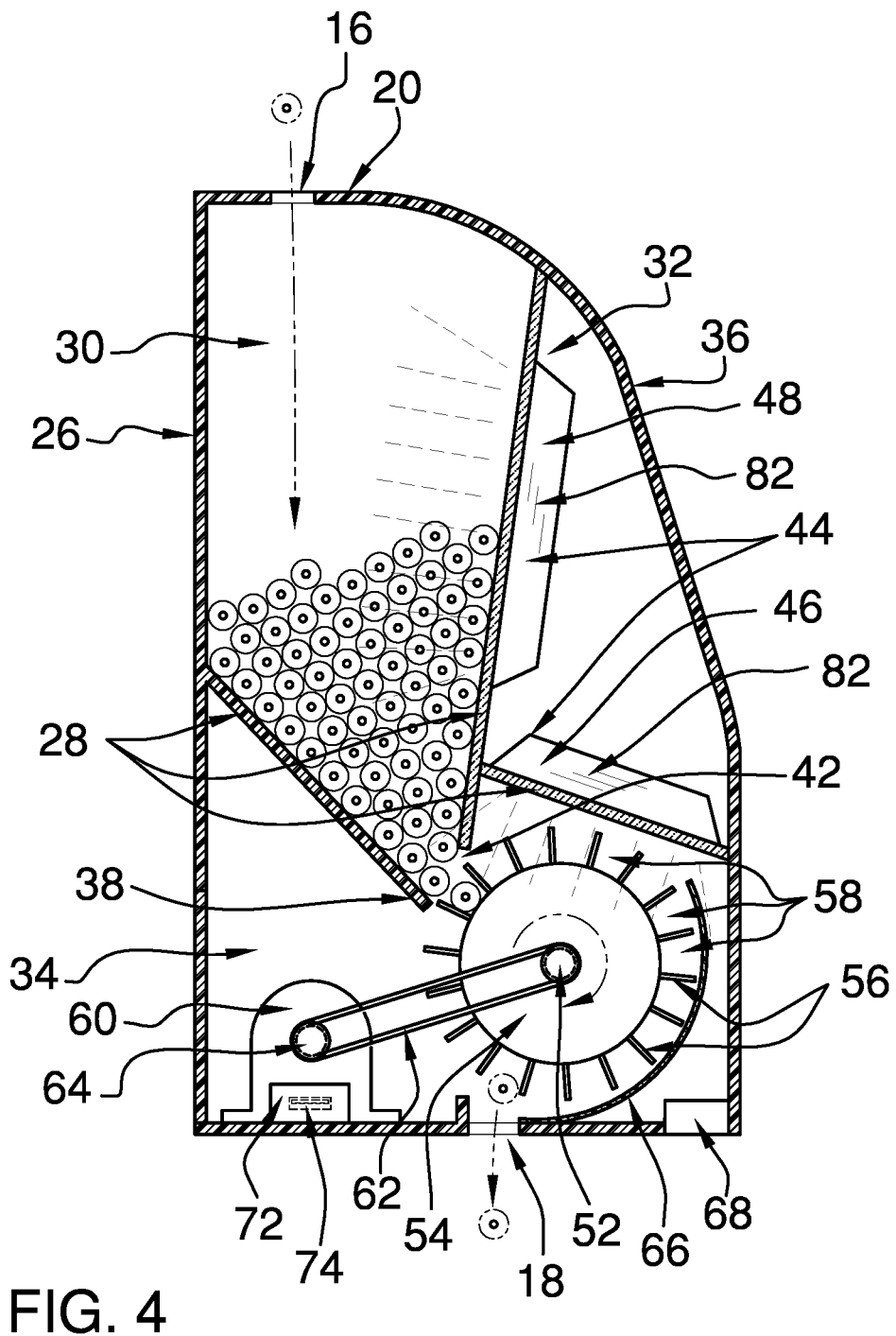
FIG. 4 is a cross-sectional view of an embodiment of the disclosure.

The back 26 of the housing 12 has an aperture 78 positioned therein, as shown in FIG. 2. The aperture 78 is configured to allow access to the interior space 14 for servicing of the dispensing unit 50. A cover panel 80 is selectively couplable to the housing 12 to close the aperture 78.

In use, the user would place their hand by the sensor 68 to obtain a sterilized writing utensil from the second slot 18, as shown in FIG. 1. Upon a writing task, the user would insert the contaminated writing utensil through the first slot 16 into the reservoir 30, as shown in FIG. 4, where it would again be sterilized.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the elements is present, unless the context clearly requires that there be only one of the elements.

I claim:

1. A sterilizing assembly comprising:
   a housing defining an interior space, the housing having a first slot and a second slot positioned in a top and a bottom thereof, respectively;
   a sanitizing unit engaged to the housing and positioned in the interior space and being configured for sterilizing a contaminated writing utensil inserted into the housing through the first slot;
   a dispensing unit engaged to the housing and positioned in the interior space and being configured for dispensing a sterilized writing utensil from the housing through the second slot;
   a sensor engaged to the bottom of the housing and being configured for detecting a presence of a hand proximate to the second slot, the sensor being operationally engaged to the dispensing unit, such that the sensor is positioned for signaling the dispensing unit to dispense the sterilized writing utensil;
   the back of the housing having an aperture positioned therein, wherein the aperture is configured for allowing access to the interior space for servicing the dispensing unit; and
   a cover panel selectively couplable to the housing for closing the aperture.

2. The sterilizing assembly of claim 1, further including the housing having a set of keyhole slots positioned in a back thereof, wherein the keyhole slots are configured for selective insertion of mounting hardware for affixing the housing to a substantially vertical surface.

3. The sterilizing assembly of claim 1, wherein the sanitizing unit comprises a light emitting diode configured for emitting ultraviolet light.

4. The sterilizing assembly of claim 1, wherein the sensor is configured for detecting motion proximate to the second slot or an object positioned proximate to the second slot.

5. The sterilizing assembly of claim 1, further including a power supply unit engaged to the housing and positioned in the interior space, the power supply unit being operationally engaged to the sanitizing unit, the dispensing unit, and the sensor, for supplying power thereto.

6. The sterilizing assembly of claim 5, wherein the power supply unit comprises an AC to DC inverter, a socket, and a power cord, the socket being positioned in a respective opposed side of the housing and being operationally engaged to the AC to DC inverter, such that the power cord is configured for operationally engaging the AC to DC inverter to a source of alternating current.

7. A sterilizing assembly comprising:
   a housing defining an interior space, the housing having a first slot and a second slot positioned in a top and a bottom thereof, respectively;
   a sanitizing unit engaged to the housing and positioned in the interior space and being configured for sterilizing a contaminated writing utensil inserted into the housing through the first slot;
   a dispensing unit engaged to the housing and positioned in the interior space and being configured for dispensing a sterilized writing utensil from the housing through the second slot;
   a sensor engaged to the bottom of the housing and being configured for detecting a presence of a hand proximate to the second slot, the sensor being operationally engaged to the dispensing unit, such that the sensor is positioned for signaling the dispensing unit to dispense the sterilized writing utensil;
   a set of panels engaged to the housing defining a reservoir, an upper chamber, and a lower chamber within the interior space;
   the first slot opening into the reservoir;
   the reservoir being positioned adjacent to the top and the back of the housing;
   the upper chamber being positioned adjacent to the top and a front of the housing;
   the lower chamber extending from the reservoir and the upper chamber to the bottom of the housing;
   respective panels separating the reservoir and the lower chamber from the upper chamber being substantially transparent; and
   the reservoir being V-shaped adjacent to a lower limit thereof, when viewed from a respective opposed side of the housing, the lower limit having a third slot positioned therein, such that the third slot fluidically engages the reservoir and the lower chamber.

8. The sterilizing assembly of claim 7, wherein the sanitizing unit comprises a first ultraviolet emitter positioned in the upper chamber and being configured for directing ultraviolet light into the lower chamber.

9. The sterilizing assembly of claim 8, wherein the first ultraviolet emitter emits at 150-170 nanometers.

10. The sterilizing assembly of claim 8, wherein the sanitizing unit comprises a second ultraviolet emitter positioned in the upper chamber and being configured for directing ultraviolet light into the reservoir.

11. The sterilizing assembly of claim 10, wherein the second ultraviolet emitter emits at 150-170 nanometers.

12. The sterilizing assembly of claim 7, wherein the dispensing unit comprises:
   an axle positioned in the lower chamber, the axle being rotationally engaged to and extending between the opposed sides of the housing;
   a hub engaged to the axle;
   a plurality of spokes engaged to and extending radially from the hub defining a plurality of channels, each channel extending longitudinally along the hub, such that the channel is positioned for receiving a respective writing utensil passing through the third slot from the reservoir into the lower chamber;
   a motor engaged to the housing and positioned in the lower chamber;
   a belt engaged to and extending between a shaft of the motor and the axle, such that the motor is positioned for selectively turning the hub for selectively aligning a respective channel with the second slot, wherein the dispensing unit is configured for dispensing a sterilized writing utensil through the second slot into the hand of a user; and
   a cover plate engaged to the housing and extending arcuately from the second slot toward the front of the housing and proximate to the plurality of spokes, wherein the cover plate is configured for retaining the sterilized writing utensil within the respective channel until the respective channel is substantially aligned with the second slot.

13. A sterilizing assembly comprising:
   a housing defining an interior space, the housing having a first slot and a second slot positioned in a top and a bottom thereof, respectively, the housing having a set of keyhole slots positioned in a back thereof, wherein the keyhole slots are configured for selective insertion of mounting hardware for affixing the housing to a substantially vertical surface;
   a set of panels engaged to the housing defining a reservoir, an upper chamber, and a lower chamber within the interior space, the first slot opening into the reservoir, the reservoir being positioned adjacent to the top and the back of the housing, the upper chamber being positioned adjacent to the top and a front of the housing, the lower chamber extending from the reservoir and the upper chamber to the bottom of the housing, respective panels separating the reservoir and the lower chamber from the upper chamber being substantially transparent, the reservoir being V-shaped adjacent to a lower limit thereof, when viewed from a respective opposed side of the housing, the lower limit having a third slot positioned therein, such that the third slot fluidically engages the reservoir and the lower chamber;
   a sanitizing unit engaged to the housing and positioned in the interior space and being configured for sterilizing a contaminated writing utensil inserted into the housing through the first slot, the sanitizing unit comprises a light emitting diode configured for emitting ultraviolet light, the sanitizing unit comprising a first ultraviolet emitter positioned in the upper chamber and being configured for directing ultraviolet light into the lower chamber, the first ultraviolet emitter emitting at 150-170 nanometers, the sanitizing unit comprising a second ultraviolet emitter positioned in the upper chamber and being configured for directing ultraviolet light into the reservoir, the second ultraviolet emitter emitting at 150-170 nanometers;

a dispensing unit engaged to the housing and positioned in the interior space and being configured for dispensing a sterilized writing utensil from the housing through the second slot, the dispensing unit comprising:
  an axle positioned in the lower chamber, the axle being rotationally engaged to and extending between the opposed sides of the housing,
  a hub engaged to the axle,
  a plurality of spokes engaged to and extending radially from the hub defining a plurality of channels, each channel extending longitudinally along the hub, such that the channel is positioned for receiving a respective writing utensil passing through the third slot from the reservoir into the lower chamber,
  a motor engaged to the housing and positioned in the lower chamber,
  a belt engaged to and extending between a shall of the motor and the axle, such that the motor is positioned for selectively turning the hub for selectively aligning a respective channel with the second slot, wherein the dispensing unit is configured for dispensing a sterilized writing utensil through the second slot into a hand of a user, and
  a cover plate engaged to the housing and extending arcuately from the second slot toward the front of the housing and proximate to the plurality of spokes, wherein the cover plate is configured for retaining the sterilized writing utensil within the respective channel until the respective channel is substantially aligned with the second slot;
a sensor engaged to the bottom of the housing and being configured for detecting a presence of the hand proximate to the second slot, the sensor being operationally engaged to the dispensing unit, such that the sensor is positioned for signaling the dispensing unit to dispense the sterilized writing utensil, the sensor being configured for detecting motion proximate to the second slot or an object positioned proximate to the second slot;
a power supply unit engaged to the housing and positioned in the interior space, the power supply unit being operationally engaged to the sanitizing unit, the dispensing unit, and the sensor, for supplying power thereto, the power supply unit comprising an AC to DC inverter, a socket, and a power cord, the socket being positioned in a respective opposed side of the housing and being operationally engaged to the AC to DC inverter, such that the power cord is configured for operationally engaging the AC to DC inverter to a source of alternating current;
the back of the housing having an aperture positioned therein, wherein the aperture is configured for allowing access to the interior space for servicing the dispensing unit; and
a cover panel selectively couplable to the housing for closing the aperture.

\* \* \* \* \*